United States Patent [19]
Ebisawa et al.

[11] Patent Number: 5,677,353
[45] Date of Patent: Oct. 14, 1997

[54] LOW-ALCOHOL PERFUME COMPOSITIONS

[75] Inventors: Toshihide Ebisawa; Yo Teshima, both of Yokohama, Japan

[73] Assignee: Shiseido Company Ltd., Tokyo, Japan

[21] Appl. No.: 490,647

[22] Filed: Jun. 15, 1995

[30] Foreign Application Priority Data

Jun. 15, 1994 [JP] Japan .................. 6-156827
Jun. 22, 1994 [JP] Japan .................. 6-163084
Mar. 29, 1995 [JP] Japan .................. 7-096152

[51] Int. Cl.$^6$ .................................................. A61K 7/32
[52] U.S. Cl. .................. 514/844; 424/65; 424/401; 512/1; 512/25; 514/848
[58] Field of Search .................. 512/1, 25; 424/401, 424/65; 514/844, 848

[56] References Cited

U.S. PATENT DOCUMENTS 4,279,891  7/1981  Henkel et al. .................. 424/73

FOREIGN PATENT DOCUMENTS 0687460  12/1995  European Pat. Off. .

*Primary Examiner*—Terressa Mosley
*Attorney, Agent, or Firm*—Townsend & Banta

[57] ABSTRACT

A low-alcohol perfume composition comprises at least 10% by weight of a single or mixed solvent of a lower glycol and/or a lower alcohol having at least 4 carbon atoms in its principal chain, not more than 40% by weight of water, and not more than 20% by weight of a perfume component. Due to the hydration characteristic of the lower glycol and the dual solvent affinity of the lower alcohol, the perfume can be dissolved. Accordingly, the amount of ethyl alcohol can be reduced without deteriorating the usability of the composition.

20 Claims, 5 Drawing Sheets

LOW-ALCOHOL PERFUME COMPOSITIONS

BACKGROUND OF THE INVENTION

1. Field of the Invention

This invention relates to low-alcohol perfume compositions and, in particular, an improvement in their solvent compositions.

2. Description of the Prior Art

In general, perfumes are seldom used alone. Before use, they are usually diluted with a solvent for perfumes which is mainly composed of ethyl alcohol.

As environmental problems have recently become a matter of much concern, restrictions on volatile organic compounds are expected in the United States. Ethyl alcohol, which is an organic solvent, is listed as one of such volatile organic compounds. In the near future, it will become necessary for alcoholic perfume compositions with a perfume content of 20% by weight or less to gradually reduce the amount of the volatile organic compound to 75% by weight or less.

However, in the case of a product with a perfume content of 15% by weight or less and an ethyl alcohol content of 75% by weight or less, for example, 10% by weight or more of the remnants should be substituted by other solvents. Such solvents have to dissolve ethyl alcohol, perfume, and other components. Also, since these solvents are used, for example, as being applied to the skin, they have to be nontoxic, less sticky, and easy to dry. Accordingly, it has been very difficult to find organic solvents with a low volatility which comply to with the above-mentioned restrictions of the volatile organic solvents. On the other hand, it has been quite difficult for a prescription to include 10% by weight or more of a compound with no flash point, such as water, without using a surface active agent.

SUMMARY OF THE INVENTION

In view of the foregoing problems of the prior art, the object of the present invention is to provide a low-alcohol perfume composition which contains a reduced amount of alcohol while maintaining the solubility and usability of the perfume composition.

As the result of industrious studies, the inventors have found that, in a low-alcohol perfume composition containing 20% by weight or less of perfume and 75% by weight or less of ethyl alcohol, its usability can be maintained when the main ingredient of the remaining solvent component for perfume comprises lower glycol and/or a lower alcohol and water. Based on this finding, the present invention has been accomplished.

According to the first aspect of the present invention, the low-alcohol perfume composition in accordance with the present invention comprises at least 10% by weight of a lower glycol, not more than 75% by weight of ethyl alcohol, not more than 40% by weight of water, and not more than 20% by weight of a perfume component.

In the second aspect of the present invention the low-alcohol perfume composition is characterized in that the composition is used for application from outside of the skin.

In the third aspect of the present invention the low-alcohol perfume composition is characterized in the amount of ethyl alcohol is 40–75% by weight and that the ratio of the lower glycol/water is within the range of 2:1 to 6:1 in the composition.

In the forth aspect of the present invention the low-alcohol perfume composition is characterized in that the lower glycol is at least one component selected from the group consisting of 1,3-butylene glycol, 1,2-propylene glycol, and 3-methyl-1,3-butane diol in the composition.

In the fifth aspect of the present invention the low-alcohol perfume composition is characterized in that the lower glycol comprises 1,3-butylene glycol and that the quantitative ratio of the lower glycol/water is within the dissolution area in the phase diagram shown in FIG. 1 in the composition.

In the sixth aspect of the present invention the low-alcohol perfume composition comprises at least 10% by weight of a lower alcohol having at least 4 carbon atoms in its principal chain, not more than 75% by weight of ethyl alcohol, not more than 40% by weight of water, and not more than 20% by weight of a perfume component.

In the seventh aspect of the present invention the low-alcohol perfume composition is characterized in the composition is used for application from outside the of skin.

In the eighth aspect of the present invention the low-alcohol perfume composition is characterized in that the amount of ethyl alcohol is 10–75% by weight and that the ratio of the lower alcohol/water is within the range of 2:3 to 4:1 in the composition.

In the ninth aspect of the present invention the low-alcohol perfume composition is characterized in that the lower alcohol comprises 3-methyl-3-methoxy butanol and that the quantitative ratio of the lower alcohol/water is within the dissolution area in the phase diagram shown in FIG. 2 in the composition, In the tenth aspect of the present invention the low-alcohol perfume composition comprises at least 10% by weight in total of a lower glycol and a lower alcohol having at least 4 carbon atoms in its principal chain, not more than 75% by weight of ethyl alcohol, not more than 40% by weight of water, and not more than 20% by weight of a perfume component.

In the eleventh aspect of the present invention the low-alcohol perfume composition is characterized in that the composition is used for application from outside of the skin.

In the twelfth aspect of the present invention the low-alcohol perfume composition is characterized in that the amount of ethyl alcohol is 10–75% by weight and that the amount of the mixed solvent formed by the lower glycol and lower alcohol is not more than 50% by weight in the composition.

In the thirteenth aspect of the present invention the low-alcohol perfume composition is characterized in that the lower glycol is at least one component selected from the group consisting of 1,3-butylene glycol, 1,2-propylene glycol, and 3-methyl-1,3-butane diol and that the lower alcohol is 3-methyl-3-methoxy butanol in the composition.

According to the above-mentioned restrictions on volatile organic compounds, the amount of the solvent becomes 85% by weight, for example, when the perfume component is 15% by weight. Since ethyl alcohol cannot be used beyond 75% by weight, at least 10% by weight of the amount of the solvent in this case has to be substituted by other solvents or the like which are not restricted. Also, as the perfume compositions may be applied directly to the skin, their safety becomes a very important requirement.

The inventors of the present invention have taken notice of lower glycols and lower alcohols having at least 4 carbon atoms in their principal chain, which have conventionally been registered materials for cosmetics as a moisture-retaining agent, and attained a very usable low-alcohol perfume composition comprising not more than 20% by weight of a perfume component and not more than 75% by weight of ethyl alcohol.

Conventionally, these lower glycols and lower alcohols have usually been compounded in cosmetics such as lotion, cleanser, and milky lotion in an amount not more than 10% by weight. They have not been used in low-alcohol perfume compositions such as those of the present invention.

According to the experiments of the inventors of the present invention, lower glycols have a function called hydration which has a high affinity to both perfume, which is structurally an oil component, and water, while lower alcohols having at least 4 carbon atoms in their principal chain have a dual solvent affinity for dissolving both oily perfume and water.

FIG. 1 shows the results of an experiment on solubility conducted by the inventors in which a rose-like perfume and, as an example of the lower glycol, 1,3-butylene glycol (1,3-B.G.) are used. As clearly understood from this drawing, when their usability is not concerned, water and 1,3-butylene glycol can dissolve the perfume without using ethyl alcohol.

Similarly, FIG. 2 shows the results of an experiment on solubility in which 3-methyl-3-methoxy butanol (MMB) is used as an example of the lower alcohol. As clearly understood from this drawing, when their usability is not concerned, water and MMB can dissolve the perfume without using ethyl alcohol.

Further, FIGS. 3–5 show the results of experiments on solubility in which 1,3-butylene glycol, as an example of the lower glycol, and 3-methyl-3-methoxy butanol, as an example of the lower alcohol, are mixed at the ratios of 1:1, 2:1, and 1:2, respectively, to form a mixed solvent. As clearly understood from these drawings, when their usability is not concerned, there exist dissolution areas when the lower glycol and lower alcohol are used as the mixed solvent.

The inventors have token notice of the affinity of lower glycols to water and the dual solvent affinity of lower alcohol compositions and accomplished the present invention.

Namely, the water content in the low-alcohol perfume compositions in accordance with the present invention is recited as not more than 40% by weight due to the dual solvent affinity of the lower alcohols and/or the hydration characteristic of the lower glycols.

Since the low-alcohol perfume compositions in accordance with the present invention contain water and the lower glycol and/or lower alcohol with a moisture-retaining function, they yield a favorable feeling of use and a moisture-retaining function when applied to skin.

BRIEF DESCRIPTIONS OF THE DRAWINGS

EXAMPLES

Figure 1:
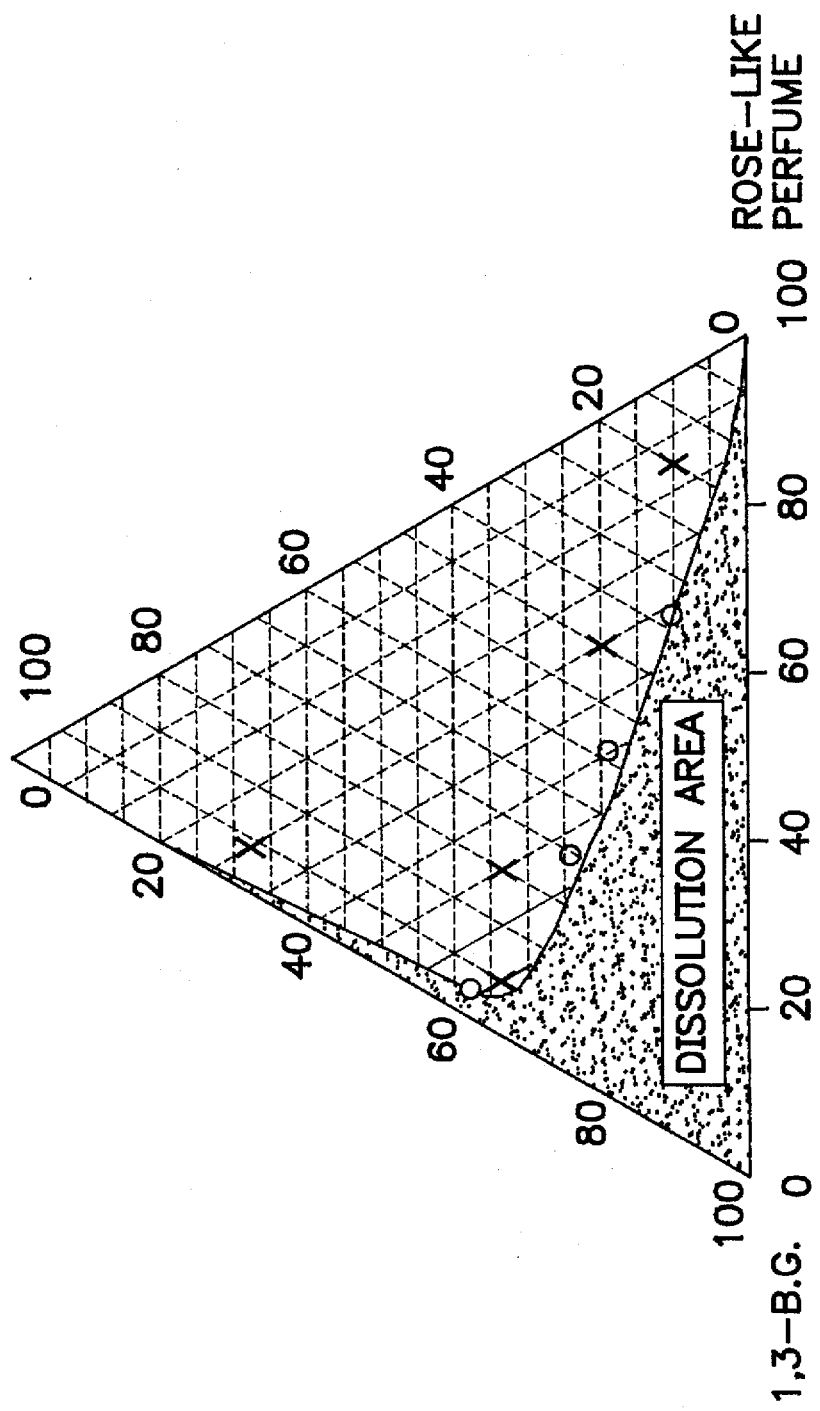
FIG. 1 is a dissolution diagram of a lower glycol, water, and a perfume.

The present invention will be explained in more detail with reference to the following examples. The amounts listed below are in percent by weight unless otherwise specified.

First, the inventors studied lower glycols as a solvent for diluting the perfume. The results are shown in TABLE 1.

TABLE 1

| Perfume | 15 | 15 | 15 | 15 | 15 | 15 |
|---|---|---|---|---|---|---|
| Ethyl alcohol | 40 | 40 | 40 | 40 | 40 | 85 |
| 1,3-butylene glycol | 30 | 0 | 0 | 45 | 0 | 0 |
| 1,2-propylene glycol | 0 | 30 | 0 | 0 | 0 | 0 |
| 3-methyl-1,3-butane diol | 0 | 0 | 30 | 0 | 0 | 0 |
| Ion-exchanged water | 15 | 15 | 15 | 0 | 45 | 0 |
| Solubility | ◎ | ◎ | ◎ | ◎ | X | ◎ |
| Quick dryness | ◎ | ◎ | Δ | Δ | — | ◎ |
| Anti-stickiness | ○ | ○ | ○ | X | — | ◎ |

As shown in the above results, the composition exhibited excellent solubility, quick dryness, and very low stickiness when ethyl alcohol was the sole component other than perfume. When the components other than perfume were constituted by 40% of ethyl alcohol, 15% of ion-exchanged water, and the remaining 1,3-butylene glycol, 1,2-propylene glycol, or 3-methyl-1,3-butane diol, the composition practically exhibited no problems though slight stickiness was perceived. Also, in particular, there were no problems concerning the quick dryness and the smell of the material when 1,3-butylene glycol or 1,2-propylene glycol was used.

In the next experiment, the inventors studied lower alcohols as a solvent for diluting the perfume. The results are shown in TABLE 2.

TABLE 2

| Perfume | 20 | 20 | 20 | 20 | 20 | 20 |
|---|---|---|---|---|---|---|
| Ethyl alcohol | 35 | 35 | 35 | 35 | 35 | 80 |
| 3-methyl-3-methoxy butanol | 30 | 0 | 0 | 45 | 0 | 0 |
| 3-methoxy-1-butanol | 0 | 30 | 0 | 0 | 0 | 0 |
| 1-methoxy-2-butanol | 0 | 0 | 30 | 0 | 0 | 0 |
| Ion-exchanged water | 15 | 15 | 15 | 0 | 45 | 0 |
| Solubility | ◎ | ◎ | ◎ | ◎ | X | ◎ |
| Quick dryness | ◎ | ◎ | ◎ | ◎ | — | ◎ |
| Anti-stickiness | ◎ | ◎ | ◎ | ○ | — | ◎ |
| Smell of solvent | ◎ | ○ | Δ | ○ | — | ◎ |

As shown in the above results, the composition exhibited excellent solubility, quick dryness, and very low stickiness when ethyl alcohol was the sole component other than perfume. When the components other than perfume were constituted by 5% of ethyl alcohol, 15% of ion-exchanged water, and the remaining lower alcohol, namely, 3-methyl-3-methoxy butanol, 3-methoxy-1-butanol, or 1-methoxy-2-butanol, though a smell of the solvent was perceived when 1-methoxy-2-butanol was used, the composition practically had no problems when the other lower alcohol compounds having at least 4 carbon atoms in their principal chain were used. Also, in particular, there were no problems concerning the quick dryness and the smell of the material when 3-methyl-3-methoxy butanol or 3-methoxy-1-butanol was used.

Then, the inventors studied the compounding ratio of the lower glycol and lower alcohol using 1,3-butylene glycol and 3-methyl-3-methoxy butanol, respectively, as their examples. The results are shown in TABLE 3.

TABLE 3

| Perfume | 20 | 20 | 20 | 20 | 20 | 20 | 20 | 20 | 20 |
|---|---|---|---|---|---|---|---|---|---|
| Ethyl alcohol | 30 | 30 | 30 | 30 | 30 | 30 | 30 | 30 | 30 |
| 1,3-butylene glycol | 30 | 29 | 25 | 20 | 15 | 10 | 5 | 1 | 0 |
| 3-methyl-3-methoxy butanol | 0 | 1 | 5 | 10 | 15 | 20 | 25 | 29 | 30 |
| Ion-exchanged water | 20 | 20 | 20 | 20 | 20 | 20 | 20 | 20 | 20 |
| Solubility | ⊚ | ⊚ | ⊚ | ⊚ | ⊚ | ⊚ | ⊚ | ⊚ | ⊚ |
| Quick-dryness | ⊚ | ⊚ | ⊚ | ⊚ | ⊚ | ⊚ | ⊚ | ⊚ | ⊚ |
| Smell of solvent | ⊚ | ⊚ | ⊚ | ⊚ | ⊚ | ⊚ | ○ | ○ | ○ |
| Anti-stickiness | ○ | ○ | ○ | ⊚ | ⊚ | ⊚ | ⊚ | ⊚ | ⊚ |

As shown in the above results, mixed solvents of the lower glycol and lower alcohol can be used in lieu of ethyl alcohol regardless of their compounding ratio. A particularly preferable compounding ratio of the lower glycol/lower alcohol is within the range of from 2:1 to 1:2.

Further, the inventors studied the composition of diluting solvents using 1,3-butylene glycol, as an example of the lower glycol. The results are shown in TABLE 4.

TABLE 4

| Perfume | 10 | 10 | 10 | 10 | 10 | 10 | 10 |
|---|---|---|---|---|---|---|---|
| Ethyl alcohol | 80 | 75 | 60 | 50 | 45 | 40 | 35 |
| 1,3-butylene glycol | 7 | 10 | 20 | 27 | 30 | 34 | 37 |
| Ion-exchanged water | 3 | 5 | 10 | 13 | 15 | 16 | 18 |
| Solubility | ⊚ | ⊚ | ⊚ | ⊚ | ⊚ | ⊚ | ⊚ |
| Quick dryness | ⊚ | ⊚ | ⊚ | ⊚ | ○ | ○ | △ |
| Anti-stickiness | ⊚ | ⊚ | ⊚ | ○ | ○ | ○ | △ |

Namely, a part of ethyl alcohol was substituted while the ratio of 1,3-butylene glycol/ion-exchanged water is fixed at about 2:1. The results show that favorable usability of the composition can be maintained even when the amount of ethyl alcohol is reduced to 40% and, more preferably, to 50%.

Then, the inventors studied the compounding ratio of 1,3-butylene glycol, as an example of the lower glycol, and ion-exchanged water. The results are shown in TABLE 5.

TABLE 5

| Perfume | 10 | 10 | 10 | 10 | 10 | 10 |
|---|---|---|---|---|---|---|
| Ethyl alcohol | 40 | 40 | 40 | 40 | 40 | 40 |
| 1,3-butylene glycol | 30 | 33 | 35 | 40 | 43 | 45 |
| Ion-exchanged water | 20 | 17 | 15 | 10 | 7 | 5 |
| Solubility | × | ○ | ○ | ⊚ | ⊚ | ⊚ |
| Quick dryness | — | ○ | ⊚ | ⊚ | ○ | ○ |
| Anti-stickiness | — | ○ | ⊚ | ⊚ | ○ | ○ |

As shown in above results, the compounding ratio of 1,3-butylene glycol/ion-exchanged water is within the range of from 2:1 to 6:1.

Further, the inventors studied the composition of diluting solvents using 3-methyl-3-methoxy butanol, as an example of the lower alcohol having at least 4 carbon atoms in its principal chain. The results are shown in TABLE 6.

TABLE 6

| Perfume | 20 | 20 | 20 | 20 | 20 | 20 | 20 | 20 |
|---|---|---|---|---|---|---|---|---|
| Ethyl alcohol | 40 | 35 | 30 | 25 | 20 | 15 | 10 | 5 |
| 3-methyl-3-methoxy butanol | 27 | 30 | 33 | 37 | 40 | 43 | 47 | 50 |
| Ion-exchanged water | 13 | 15 | 17 | 18 | 20 | 22 | 23 | 25 |
| Solubility | ⊚ | ⊚ | ⊚ | ⊚ | ⊚ | ⊚ | ⊚ | ⊚ |
| Quick dryness | ⊚ | ⊚ | ⊚ | ⊚ | ○ | ○ | ○ | ○ |
| Smell of solvent | ⊚ | ⊚ | ⊚ | ⊚ | ○ | △ | △ | △ |
| Anti-stickiness | ⊚ | ⊚ | ⊚ | ○ | ○ | ○ | △ | △ |

Namely, a part of ethyl alcohol was substituted while the ratio of 3-methyl-3-methoxy butanol/ion-exchanged water is fixed at about 2:1. The results show that favorable usability of the composition can be maintained even when the amount of ethyl alcohol is reduced to 10% and, more preferably, to 20%.

Then, the inventors studied the compounding ratio of 3-methyl-3-methoxy butanol, as an example of lower alcohol at least 4 carbon atoms in its principal chain, and ion-exchanged water. The results are shown in TABLE 7.

TABLE 7

| Perfume | 20 | 20 | 20 | 20 | 20 | 20 | 20 | 20 |
|---|---|---|---|---|---|---|---|---|
| Ethyl alcohol | 30 | 30 | 30 | 30 | 30 | 30 | 30 | 30 |
| 3-methyl-3-methoxy butanol | 10 | 15 | 20 | 25 | 30 | 35 | 40 | 45 |
| Ion-exchanged water | 40 | 35 | 30 | 25 | 20 | 15 | 10 | 5 |
| Solubility | × | × | ○ | ⊚ | ⊚ | ⊚ | ⊚ | ⊚ |
| Quick dryness | — | — | ⊚ | ⊚ | ⊚ | ⊚ | ○ | ○ |
| Smell of solvent | — | — | ⊚ | ⊚ | ⊚ | ⊚ | ○ | △ |
| Anti-stickiness | — | — | ⊚ | ⊚ | ⊚ | ○ | ○ | ○ |

As shown in above results, the compounding ratio of 3-methyl-3-methoxy butanol/ion-exchanged water is within the range of from 2:3 to 4:1.

Further, the inventors studied the composition of diluting solvents using 1,3-butylene glycol, as an example of the lower glycol, and 3-methyl-3-methoxy butanol, as an example of the lower alcohol having at least 4 carbon atoms in its principal chain, to make a mixed solvent with their mixing ratio of 1:1. The results are shown in TABLE 8.

TABLE 8

| Perfume | 20 | 20 | 20 | 20 | 20 | 20 | 20 | 20 |
|---|---|---|---|---|---|---|---|---|
| Ethyl alcohol | 40 | 35 | 30 | 25 | 20 | 15 | 10 | 5 |
| Mixed solvent | 25 | 30 | 33 | 37 | 40 | 43 | 46 | 50 |
| Ion-exchanged water | 15 | 15 | 17 | 18 | 20 | 22 | 24 | 25 |
| Solubility | ⊚ | ⊚ | ⊚ | ⊚ | ⊚ | ⊚ | ⊚ | ⊚ |
| Quick-dryness | ⊚ | ⊚ | ⊚ | ⊚ | ○ | ○ | ○ | ○ |
| Smell of solvent | ⊚ | ⊚ | ⊚ | ⊚ | ○ | △ | △ | △ |
| Anti-stickiness | ⊚ | ⊚ | ⊚ | ○ | ○ | ○ | △ | × |

Namely, a part of ethyl alcohol was substituted while the ratio of the mixed solvent/ion-exchanged water is fixed at about 2:1. The results show that favorable usability of the composition can be maintained even when the amount of ethyl alcohol is reduced to 10% and, more preferably, to 20%.

Then, the inventors studied the compounding ratio of water by using a mixed solvent comprising 1,3-butylene glycol and 3-methyl-3-methoxy butanol with their mixing ratio of 1:1. The results are shown in TABLE 9 to TABLE 11.

TABLE 9

| Perfume | 20 | 20 | 20 | 20 | 20 | 20 | 20 | 20 | 20 | 20 |
|---|---|---|---|---|---|---|---|---|---|---|
| Ethyl alcohol | 70 | 60 | 60 | 50 | 50 | 50 | 40 | 40 | 40 | 40 |
| Mixed solvent | 10 | 20 | 10 | 30 | 20 | 10 | 40 | 30 | 20 | 10 |
| Ion-exchanged water | 0 | 0 | 10 | 0 | 10 | 20 | 0 | 10 | 20 | 30 |
| Solubility | ⊚ | ⊚ | ⊚ | ⊚ | ⊚ | ⊚ | ⊚ | ⊚ | ⊚ | ⊚ |
| Quick-dryness | ⊚ | ⊚ | ⊚ | ⊚ | ⊚ | ⊚ | ○ | ⊚ | ⊚ | ⊚ |
| Smell of solvent | ⊚ | ⊚ | ⊚ | ⊚ | ⊚ | ⊚ | ○ | ○ | ⊚ | ⊚ |
| Anti-stickiness | ⊚ | ⊚ | ⊚ | ⊚ | ⊚ | ⊚ | ○ | ⊚ | ⊚ | ⊚ |

TABLE 10

| Perfume | 20 | 20 | 20 | 20 | 20 | 20 | 20 | 20 | 20 |
|---|---|---|---|---|---|---|---|---|---|
| Ethyl alcohol | 30 | 30 | 30 | 30 | 30 | 20 | 20 | 20 | 20 |
| Mixed solvent | 50 | 40 | 30 | 20 | 10 | 60 | 50 | 40 | 30 | 20 |

TABLE 10-continued

| | | | | | | | | | | |
|---|---|---|---|---|---|---|---|---|---|---|
| Ion-exchanged water | 0 | 10 | 20 | 30 | 40 | 0 | 10 | 20 | 30 | 40 |
| Solubility | ◉ | ◉ | ◉ | ◉ | ◉ | ◉ | ◉ | ◉ | ◉ | ◉ |
| Quick dryness | o | o | ◉ | ◉ | ◉ | Δ | o | o | o | ◉ |
| Smell of solvent | Δ | Δ | ◉ | ◉ | ◉ | Δ | Δ | Δ | o | ◉ |
| Anti-stickiness | X | Δ | o | ◉ | ◉ | X | X | Δ | o | ◉ |

TABLE 11

| | | | | | | | | |
|---|---|---|---|---|---|---|---|---|
| Perfume | 20 | 20 | 20 | 20 | 20 | 20 | 20 | 20 |
| Ethyl alcohol | 20 | 10 | 10 | 10 | 10 | 10 | 10 | 10 |
| Mixed solvent | 10 | 70 | 60 | 50 | 40 | 30 | 20 | 10 |
| Ion-exchanged water | 50 | 0 | 10 | 20 | 30 | 40 | 50 | 60 |
| Solubility | X | ◉ | ◉ | ◉ | ◉ | ◉ | X | X |
| Quick dryness | — | Δ | o | o | o | o | — | — |
| Smell of solvent | — | Δ | o | o | o | o | — | — |
| Anti-stickiness | — | Δ | o | o | o | o | — | — |

As shown in TABLE 9 to TABLE 11, favorable usability of the composition could be maintained when not more than 50%, or more preferably not more than 40%, by weight of the 1:1 mixed solvent of 1,3-butylene glycol and 3-methyl-3-methoxy butanol was compounded therein. When water exceeded 40% by weight, the usability of the composition was deteriorated due to problems in solubility. Accordingly, the amount of water should be limited to 40% by weight or less.

As described in the foregoing, both product value and usability can be sufficiently maintained when the compounding amounts of lower glycol or/and lower alcohol, ion-exchanged water, and ethyl alcohol are appropriately selected.

Thus, when the perfume composition is made within the range where the total amount of lower glycol, lower alcohol, and ion-exchanged water is at least 10% by weight, the amount of ethyl alcohol can be reduced while maintaining the usability of the composition.

These tendencies are observed when the amount of the perfume is up to about 50% by weight.

While there has been described what is at present considered to be a preferred embodiment of the invention, it should be understood that various modifications my be made thereto, and it should be understood that the appended claims cover all such modifications which fall within the true spirit and scope of the present invention.

What is claimed is:

1. A low-alcohol perfume composition comprising at least 10% by weight of a lower glycol, not more than 75% by weight of ethyl alcohol, not more than 40% by weight of water, and not more than 20% by weight of a perfume component.

2. Applying to the skin a low-alcohol perfume composition comprising at least 10% by weight of a lower glycol, not more than 75% by weight of ethyl alcohol, not more than 40% by weight of water, and not more than 20% by weight of a perfume component.

3. A low-alcohol perfume composition according to claim 1 in which the amount of ethyl alcohol is 40–75% by weight and the ratio of the lower glycol/water is within the range of from 2:1 to 6:1.

4. A low-alcohol perfume composition according to claim 1 in which the lower glycol is at least one component selected from the group consisting of 1,3-butylene glycol, 1,2-propylene glycol, and 3-methyl-1,3-butane diol.

5. A low-alcohol perfume composition according to claim 1 in which the lower glycol comprises 1,3-butylene glycol and the quantitative ratio of the lower glycol/water is within a dissolution area in the phase diagram of FIG. 1.

6. A low-alcohol perfume composition comprising at least 10% by weight of a lower alcohol having at least 4 carbon atoms in its principal chain, not more than 75% by weight of ethyl alcohol, not more than 40% by weight of water, and not more than 20% by weight of a perfume component.

7. Applying to the skin a low-alcohol perfume composition comprising at least 10% by weight of a lower alcohol having at least 4 carbon atoms in its principal chain, not more than 75% by weight of ethyl alcohol, not more than 40% by weight of water, and not more than 20% by weight of a perfume component.

8. A low-alcohol perfume composition according to claim 6 in which the amount of ethyl alcohol is 10–75% by weight and the ratio of the lower alcohol/water is within the range of from 2:3 to 4:1.

Figure 2:
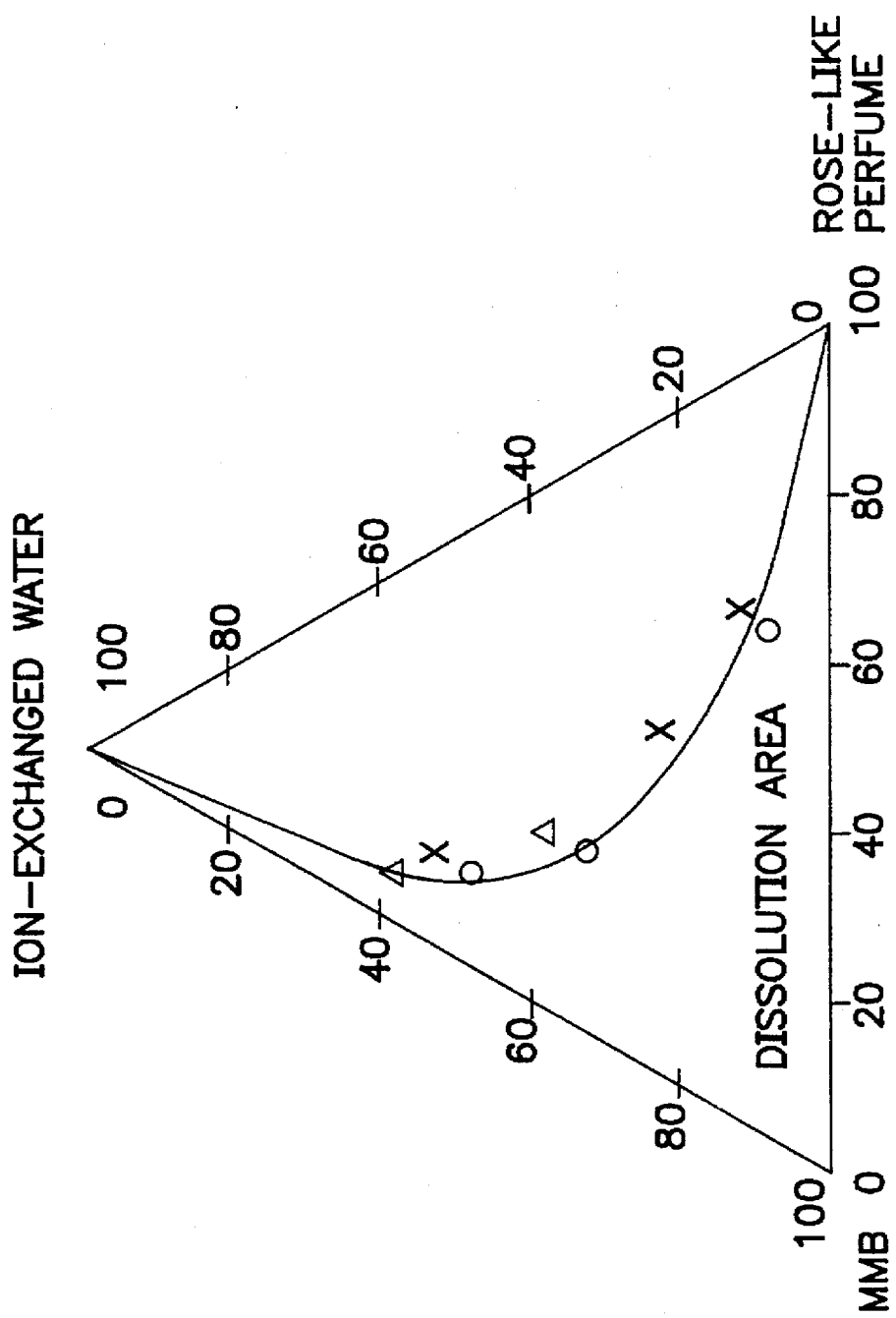
FIG. 2 is a dissolution diagram of a lower alcohol, water, and a perfume.
Figure 3:
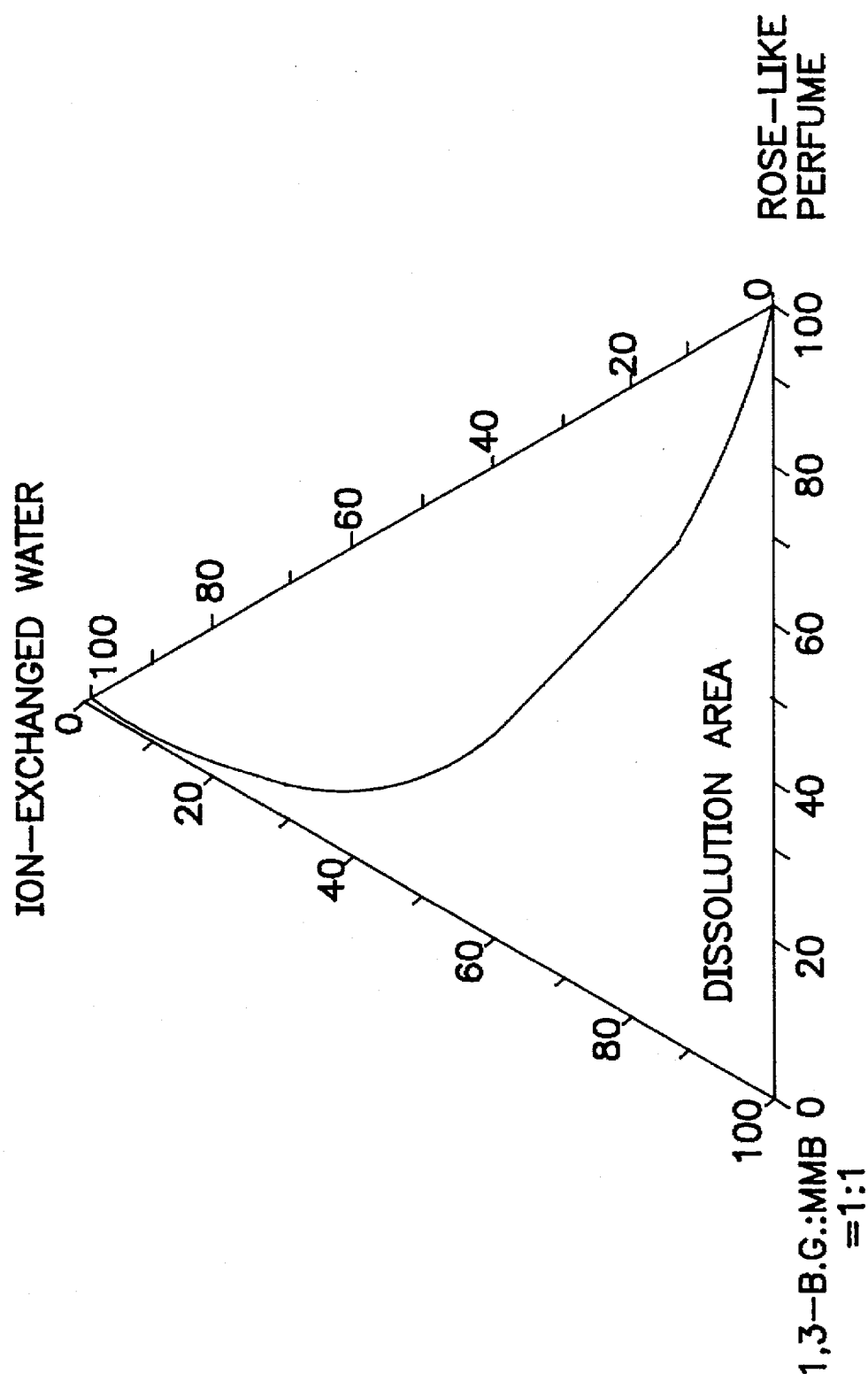
FIG. 3 is a dissolution diagram of a mixed solvent with the ratio of lower glycol/lower alcohol at 1:1, water, and a perfume.
Figure 4:
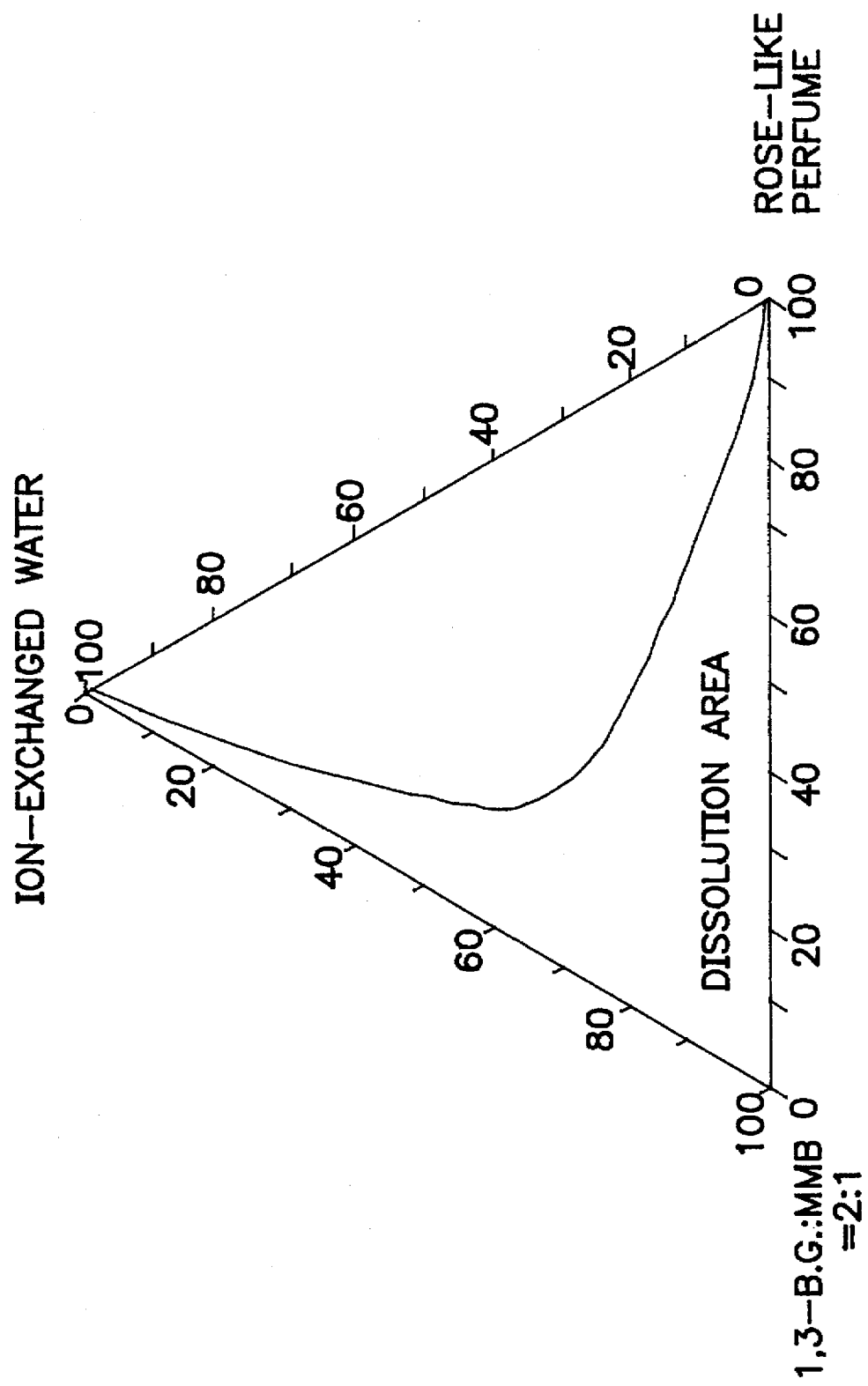
FIG. 4 is a dissolution diagram of a mixed solvent with the ratio of lower glycol/lower alcohol at 2:1, water, and a perfume.
Figure 5:
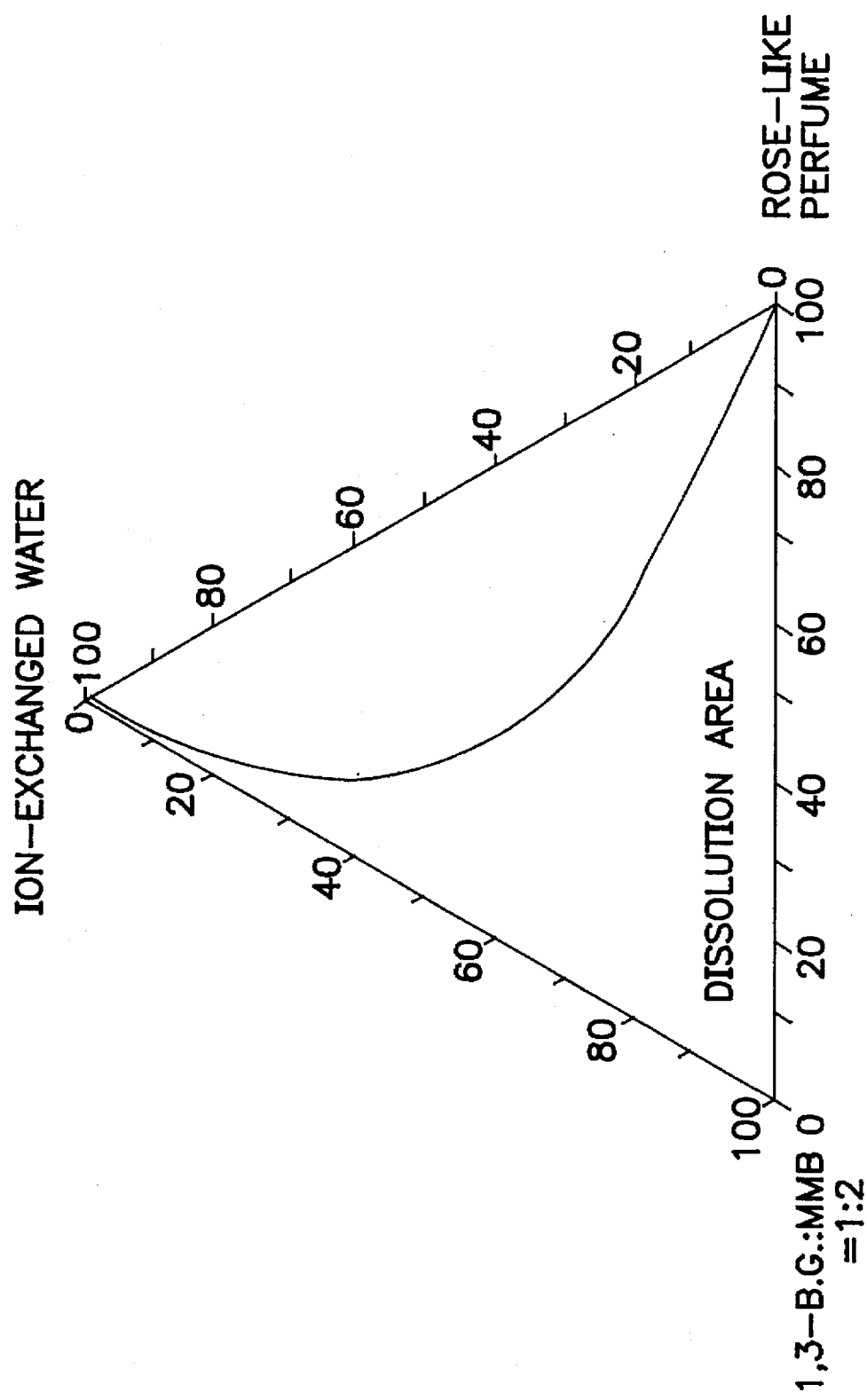
FIG. 5 is a dissolution diagram of a mixed solvent with the ratio of lower glycol/lower alcohol at 1:2, water, and a perfume.

9. A low-alcohol perfume composition according to claim 6 in which the lower alcohol comprises 3-methyl-3-methoxy butanol and the quantitative ratio of the lower alcohol/water is within a dissolution area in the phase diagram of FIG. 2.

10. A low-alcohol perfume composition comprising at least 10% by weight in total of a lower glycol and a lower alcohol having at least 4 carbon atoms in its principal chain, not more than 75% by weight of ethyl alcohol, not more than 40% by weight of water, and not more than 20% by weight of a perfume component.

11. Applying to the skin a low-alcohol perfume composition comprising at least 10% by weight in total of a lower glycol and a lower alcohol having at least 4 carbon atoms in its principal chain, not more than 75% by weight of ethyl alcohol, not mote than 40% by weight of water, and not more than 20% by weight of a perfume component.

12. A low-alcohol perfume composition according to claim 10 in which the amount of ethyl alcohol is 10–75% by weight and the amount of the mixed solvent formed by the lower glycol and lower alcohol is not more than 50% by weight.

13. A low-alcohol perfume composition according to claim 10 in which the lower glycol is at least one component selected from the group consisting of 1,3-butylene glycol, 1,2-propylene glycol, and 3-methyl-1,3-butane diol and the lower alcohol is 3-methyl-3-methoxy butanol.

14. Applying to the skin a low-alcohol perfume composition as in claim 2 wherein the amount of ethyl alcohol is 40–75% by weight and the ratio of the lower glycol/water is within the range of from 2:1 to 6:1.

15. Applying to the skin a low-alcohol perfume composition as in claim 2 wherein the lower glycol is at least one component selected from the group consisting of 1,3-butylene glycol, 1,2-propylene glycol, and 3-methyl-1,3-butane diol.

16. Applying to the skin a low-alcohol perfume composition as in claim 2 wherein the lower glycol comprises 1,3-butylene glycol and the ratio of the lower glycol/water is within a dissolution area in the phase diagram of FIG. 1.

17. Applying to the skin a low-alcohol perfume composition of claim 7, wherein the amount of ethyl alcohol is 10–75% by weight and the ratio of the lower alcohol/water is within the range of from 2:3 to 4:1.

18. Applying to the skin a low-alcohol perfume composition as in claim 7, wherein the lower alcohol comprises 3-methyl-3-methoxy butanol and the ratio of the lower alcohol/water is within a dissolution area in the phase diagram of FIG. 2.

19. Applying to the skin a low-alcohol perfume composition as in claim 11 wherein the amount of ethyl alcohol is 10–75% by weight and the amount of mixed solvent formed by the lower glycol and lower alcohol is not more than 50% by weight.

20. Applying to the skin a low-alcohol perfume composition as in claim 11, wherein the lower glycol is at least one component selected from the group consisting of 1,3-butylene glycol, 1,2-propylene glycol, and 3-methyl-1,3-butane diol, and the lower alcohol is 3-methyl-3-methoxy butanol.

* * * * *